United States Patent [19]

Rose et al.

[11] 4,171,203

[45] Oct. 16, 1979

[54] HAIR DYE COMPOSITIONS CONTAINING 3,5-DIAMINO-2-SUBSTITUTED-ALKYLBENZENES

[75] Inventors: David Rose, Hilden; Erwin Weinrich, Haan; Edgar Lieske, Dudseldorf, all of Fed. Rep. of Germany

[73] Assignee: Henkel Kommanditgesellschaft auf Aktien, Dusseldorf-Holthausen, Fed. Rep. of Germany

[21] Appl. No.: 807,972

[22] Filed: Jun. 20, 1977

[30] Foreign Application Priority Data

Jun. 28, 1976 [DE] Fed. Rep. of Germany ....... 2628999

[51] Int. Cl.² .................. A61K 7/13; C07C 91/42; C07C 93/14
[52] U.S. Cl. .................................. 8/10.2; 8/11; 8/32; 260/571; 260/575
[58] Field of Search .................. 8/10.2, 11, 32; 260/571, 575

[56] References Cited

U.S. PATENT DOCUMENTS

| | | | |
|---|---|---|---|
| 1,574,337 | 2/1926 | Bogert | 260/571 |
| 2,548,574 | 4/1951 | Weissberger et al. | 260/574 X |
| 3,210,252 | 10/1965 | Blanke et al. | 8/10.2 |
| 3,413,073 | 11/1968 | Bugant et al. | 8/11 |
| 3,563,684 | 2/1971 | Charle et al. | 8/11 |
| 3,576,876 | 4/1971 | Raper et al. | 260/575 |
| 3,649,160 | 3/1972 | Kalopissis et al. | 8/10.2 |
| 3,712,790 | 1/1973 | Kaloppissis et al. | 8/10.2 |
| 3,884,627 | 5/1975 | Brody et al. | 8/10.2 |
| 4,003,699 | 1/1977 | Rose et al. | 8/10.2 |
| 4,031,160 | 6/1977 | Kalopissis et al. | 260/575 |
| 4,065,255 | 12/1977 | Andrillon et al. | 8/10.2 |

Primary Examiner—James O. Thomas, Jr.
Assistant Examiner—Vera C. Clarke
Attorney, Agent, or Firm—Hammond & Littell

[57] ABSTRACT

Dyestuffs of the oxidizable developer-coupler type wherein the coupler is a 3,5-diamino-2-substituted-alkylbenzene of the formula

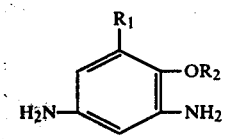

wherein $R_1$ is straight- or branched-chain alkyl of 1–8 carbon atoms, $R_2$ is a straight- or branched-chain alkyl of 1–8 carbon atoms, phenyl, or phenyl substituted by alkyl of 1–4 carbon atoms or halogen atoms and the inorganic and organic salts thereof are very satisfactory for coloring hair. They are readily oxidized by atmospheric oxygen at room temperature without a catalyst, and they provide intense, bright and fast dyeings in a short tie. They are applied in conventional manner from an aqueous medium.

20 Claims, No Drawings

HAIR DYE COMPOSITIONS CONTAINING 3,5-DIAMINO-2-SUBSTITUTED-ALKYLBENZENES

FIELD OF THE INVENTION

The present invention relates to oxidizable developer-coupler dyestuff combinations for the dyeing of hair wherein the coupler component is a 3,5-diamino-2-substituted-alkyl benzene. The invention includes the developer-coupler combinations themselves, preparations for the dyeing of hair wherein the dye component includes the aforesaid developer-coupler combinations, and the processes involved.

THE PRIOR ART

Of great importance for the dyeing of hair are the so-called oxidation dyestuffs because of their intensive colors and very good fastness. These dyestuffs are formed by the oxidative coupling of a developer component with a coupling component. The developers customarily used are nitrogenous bases, such as p-phenylenediamine derivatives, diaminopyridines, 4-aminopyrazolone derivatives or heterocyclic hydrazones. Useful as so-called coupling components are m-phenylenediamine derivatives, phenols, naphthols, resorcinol derivatives and pyrazolones.

Good oxidation dyestuff components for hair dyeing must primarily meet the following requirements.

They have to be able to develop a sufficient intensity of the desired color shades when oxidatively coupled with the respective developer component or coupling component. Furthermore, they have to possess a capacity for being absorbed by human hair, which capacity ranges from sufficient to very good; and in addition, they should be unobjectionable from toxicological and dermatological viewpoints. Furthermore, it is important to obtain vivid color shades on the hair to be dyed, corresponding as far as possible to the natural hair shades. The intensive yellow and brown color shades are particularly desirable color tones. Furthermore, the stability of the dyeings effected (their light-fastness, wash-fastness and thermostability) are of great importance in order to avoid shifts from the original color nuance, or even changes to other color tones.

The problem in the search for suitable oxidation hair dyes was therefore to find suitable components which best meet the above-mentioned requirements.

OBJECTS OF THE INVENTION

An object of the invention is to provide usable oxidation hair dyes containing suitable components which optimally satisfy the above requirements.

Another object of the present invention is to provide an oxidation dyestuff combination of a developer component and a coupling component, which is based on a 3,5-diamino-2-substituted-alkyl benzene as the coupler component.

A still further object is to provide oxidation dyestuff combinations of a developer component and a coupling component of especially good properties, which are based on a 3,5-diamino-2-substituted-alkyl benzene as the coupler component and a tetraaminopyrimidine or p-toluenediamine as the developer component.

These and further objects of the present invention will become apparent as the description thereof proceeds.

DESCRIPTION OF THE INVENTION

The discovery has now been made that the above objects are attained in a very satisfactory manner when the coupler component in a developer-coupler hair dye composition is a 3,5-diamino alkyl benzene substituted in the 2-position of the formula

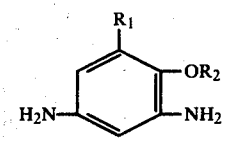

wherein $R_1$ is a straight- or branched-chain alkyl radical of 1 to 8 carbon atoms, and $R_2$ is a member selected from the group consisting of a straight- or branched-chain alkyl radical of 1 to 8 carbon atoms, phenyl, and phenyl substituted by a member selected from the group consisting of alkyl radicals of 1 to 4 carbon atoms and halogen atoms, or an inorganic or organic acid salt thereof.

$R_2$ as phenyl can advantageously be substituted by 1–3 alkyl or halogen substituents, more preferably by 1–2 such substituents. Methyl and chloro may be mentioned as two such very suitable substituents.

The above 3,5-diamino-2-substituted-alkyl benzenes, when applied in conjunction with conventional developers generally used for oxidation hair dyeing, provide very intensive yellow and brown color shades and thus constitute a substantial enrichment of the art of oxidation hair dyeing. Beyond this, these 3,5-diamino-2-substituted alkyl benzenes and their water-soluble salts are distinguished by good fastness properties in the colorings achieved with them, by good solubility in water, good storability, and toxicological and dermatological harmlessness.

The 3,5-diamino-2-substituted-alkyl benzenes to be used as coupler components according to the invention can be used either as such or in the form of their salts with inorganic or organic acids, such as chlorides, sulfates, phosphates, acetates, propionates, lactates, citrates, etc.

The new 3,5-diamino-2-substituted-alkyl benzenes of the invention can be prepared according to known methods, as e.g. by catalytic reduction of the corresponding 3,5-dinitro-2-substituted alkyl benzenes by means of hydrogen and palladium on carbon as the catalyst.

Compounds suitable for use as coupler components according to the invention are, for example: 3,5-diamino-2-methoxytoluene, 3,5-diamino-2-ethoxytoluene, 3,5-diamino-2-propoxytoluene, 3,5-diamino-2-butoxytoluene, 3,5-diamino-2-octoxytoluene, 3,5-diamino-2-oxy(2-ethylhexyl)toluene, 3,5-diamino-2-phenoxytoluene, 3,5-diamino-2-(4'-methylphenoxy)toluene, 3,5-diamino-2-(4'-chlorophenoxy)-toluene, 3,5-diamino-2-(2', 4'-dimethylphenoxy)toluene, 3,5-diamino-2-(2',4'-dichlorophenoxy)toluene, 3,5-diamino-2-methoxyethylbenzene, 3,5-diamino-2-ethoxyethylbenzene, 3,5-diamino-2-butoxy-ethylbenzene, 3,5-diamino-2-phenoxyethylbenzene, 3,5-diamino-2-methoxy-n-propylbenzene, 3,5-diamino-2-methoxy-i-propylbenzene, 3,5-diamino-2-ethoxy-n-propylbenzene, 3,5-diamino-2-butoxy-i-propyl-benzene, 3,5-diamino-2-methoxy-tert.-butylbenzene, 3,5-diamino-2-ethoxy-tert.-butylbenzene, 3,5-diamino-2-methoxy-2'-ethylhexylbenzene, 3,5-diamino-2-phenoxyhexylbenzene, 3,5-diamino-2-methoxyoctylbenzene, 3,5-diamino-2-ethoxyoctylbenzene, 3,5-diamino-2-phenoxyoctylbenzene, 3,5-diamino-2-(4'-chlorophenoxy)-octylbenzene.

Among the 3,5-diamino-2-substituted-alkyl benzenes to be used as coupler components in accordance with the invention, preferred are those compounds wherein $R_1$ and $R_2$ are alkyl radicals with 1–4 carbon atoms, such as 3,5-diamino-2-methoxytoluene, 3,5-diamino-2-ethoxytoluene, 3,5-diamino-2-propoxytoluene, 3,5-diamino-2-butoxytoluene, 3,5-diamino-2-methoxyethylbenzene, 3,5-diamino-2-methoxypropylbenzene, 3,5-diamino-2-methoxy-i-propylbenzene, 3,5-diamino-2-methoxybutylbenzene, 3,5-diamino-2-ethoxyethylbenzene, 3,5-diamino-2-ethoxypropylbenzene, 3,5-diamino-2-ethoxybutylbenzene, 3,5-diamino-2-propoxyethylbenzene, 3,5-diamino-2-propoxybutylbenzene, 3,5-diamino-2-butoxyethylbenzene and 3,5-diamino-2-butoxy-i-propylbenzene. The most important coupling component among these compounds is 3,5-diamino-2-methoxytoluene.

As examples of the developer components to be used in the hair dyes according to the invention are the primary aromatic amines with an additional functional group in the para-position, such as p-phenylene-diamine, p-toluenediamine, p-(dimethylamino) aniline, p-aminophenol, p-diaminoanisole and other compounds of the above-mentioned type, which can contain one or more additional functional groups like OH groups, $-NH_2$ groups, $-NHR$ groups, and $-NR_2$ groups, where R is an alkyl or hydroxyalkyl radical with 1–4 carbon atoms; also diaminopyridine derivatives, heterocyclic hydrazone derivatives, and 4-aminopyrazolone derivatives, such as 4-amino-1-phenyl-3-carbamoylpyrazolone-5.

Of particular importance is the combination of the 3,5-diamino-2-substituted-alkyl benzenes as coupler components with (A) tetraaminopyrimidines of the formula

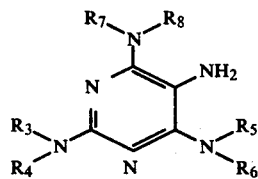

wherein $R_3$, $R_4$, $R_5$, $R_6$, $R_7$ and $R_8$ are each selected from the group consisting of hydrogen, phenyl, alkyl having 1 to 4 carbon atoms, phenylalkyl having 7 to 10 carbon atoms, phenylalkenyl having 7 to 10 carbon atoms, $$X-(CH_2)_n-$$

wherein n is an integer from 1 to 4, and X is selected from the group consisting of hydroxyl, halogen and $NR_9R_{10}-$ in which $R_9$ and $R_{10}$ are each independently hydrogen or alkyl having 1 to 4 carbon atoms, and together with the nitrogen atom $R_9$ and $R_{10}$ can form a heterocyclic ring optionally containing an additional nitrogen atom or oxygen atom, and wherein $R_3$ and $R_4$, $R_5$ and $R_6$, and $R_7$ and $R_8$, together with the nitrogen atom can form a five to six membered heterocyclic ring optionally containing another nitrogen or oxygen atom in the ring and (B) water-soluble inorganic or organic acid addition salts of (A).

$R_9$ and $R_{10}$ can advantageously form a member selected from the group consisting of a 5 to 6 membered heterocyclic ring optionally containing an additional nitrogen atom or oxygen atom.

Examples of groups which can be formed by $R_3$ and $R_4$, $R_5$ and $R_6$, $R_7$ and $R_8$, and $R_9$ and $R_{10}$ are tetramethylene, pentamethylene, azatetramethylene, azapentamethylene, oxatetramethylene, and oxapentamethylene.

A particularly preferred subgenus of the above-mentioned developer component is wherein $R_3$, $R_4$, $R_5$, $R_6$, $R_7$ and $R_8$ are each selected from the group consisting of hydrogen, methyl, ethyl, isopropyl, n-propyl, butyl, phenyl, benzyl and benzylidene, or $-(CH_2)_n-X$, and wherein $R_3$ and $R_4$, or $R_5$ and $R_6$, or $R_7$ and $R_8$, together with the nitrogen atom form a substituent selected from the group consisting of piperidino and morpholino; and wherein n is 1, 2 or 3 and X is selected from the group consisting of hydroxyl, halogen and $-NR_9R_{10}$ in which $R_9$ and $R_{10}$ are each hydrogen or alkyl having 1 to 4 carbon atoms.

The above tetraaminopyrimidines are disclosed in U.S. Pat. No. 4,003,699, the teachings of which are incorporated herein by reference.

The tetraaminopyrimidines which are to be used as developer components according to the invention can be used either as such or in form of their acid addition salts with non-toxic inorganic acids or organic acids, such as for example, hydrochloric acid, sulfuric acid, phosphoric acid, acetic acid, propionic acid, lactic acid or citric acid.

The preparation of most tetraaminopyrimidines to be used as developer components according to the invention is already known in the literature and can be taken from the monograph by D. J. Brown, in the series "Heterocyclic Compounds", Interscience Publishers, 1962, Vols. I and II, "The Pyrimidines". The preparation of some of the tetraaminopyrimidines of the invention is disclosed in U.S. Pat. No. 4,003,699.

The synthesize the tetraaminopyrimidine compounds to be used according to the invention, the starting material generally is a 2,4,6-aminopyrimidine, into which the 5-amino group is introduced by nitrosation and subsequent reduction. It is also possible to start from the correspondingly substituted triaminoalkylmercaptopyrimidines and to replace the alkylmercapto group with an amino group. The latter method is especially suitable for the introduction of amino groups (or substituted amino groups) into the 2-, 4-, or 6-positions of the pyrimidine ring.

Suitable examples of tetraaminopyrimidines to be used in combination with the 3,5-diamino-2-substituted alkyl benzenes in the hair dyes according to the invention are 2,4,5,6-tetraamino-pyrimidine, 4,5-diamino-2,6-bis(methylamino)-pyrimidine, 2,5-diamino-4,6-bis(methylamino)-pyrimidine, 4,5-diamino-6-(butylamino)-2-(dimethylamino)-pyrimidine, 2,5-diamino-4-(diethylamino)-6-(methylamino)-pyrimidine, 4,5-diamino-6-(diethylamino)-(2-dimethylamino)-pyrimidine, 4,5-diamino-2-(diethylamino)-6-(methylamino)-pyrimidine, 4,5-diamino-2-(dimethylamino)-6-(ethylamino)-pyrimidine, 4,5-diamino-2-(dimethylamino)-6-(isopropylamino)-pyrimidine, 4,5-diamino-2-(dimethylamino)-6-(methylamino)-pyrimidine, 4,5-diamino-6-(dimethylamino)-2-(methylamino)-pyrimidine, 4,5-diamino-2-(dimethylamino)-6-(propylamino)-pyrimidine, 2,4,5-triamino-6-(dimethylamino)-pyrimidine, 4,5,6-triamino-2-(dimethylamino)-pyrimidine, 2,4,5- triamino-6-(methylamino)pyrimidine, 4,5,6-triamino-2-(methylamino)pyrimidine, 4,5-diamino-2-(dimethylamino)-6-piperidinopyrimidine, 4,5-diamino-6-(methylamino)-2-piperidino-pyrimidine, 2,4,5-triamino-6-piperidino-pyrimidine, 2,4,5-triamino-6-anilino-pyrimidine, 2,4,5-triamino-6-(benzylamino)-pyrimidine, 2,4,5-triamino-6-(benzylideneamino)-pyrimidine, 4,5,6-triamino-2-piperidino-pyrimidine, 5-amino-2,4,6-tris-(methylamino)-pyrimidine, 2,4,5-triamino-6-(di-n-propylamino)pyrimidine, 2,4,5-triamino-6-morpholino-pyrimidine, 2,5,6-triamino-4-(dimethylamino)-pyrimidine, 4,5,6-triamino-2-morpholino-pyrimidine, 2,4,5-triamino-6-(β-hydroxyethylamino)pyrimidine, 4,5,6-triamino-2-[(β-aminoethyl)amino]-pyrimidine, 2,5,6-triamino-4-[(β-methylamino)-ethylamino]pyrimidine, 2,5-diamino-4,6-[bis-(γ-diethylamino)-propylamino]-pyrimidine, 4,5-diamino-6-[(β-hydroxyethyl)-amino]-2-(methylamino)pyrimidine, 5-amino-2,4,6-(triethylamino)-pyrimidine, and 5-amino-6-anilino-2,4-[bis-(β-hydroxyethyl)-amino]pyrimidine.

When used as developer components, the tetraaminopyrimidines yield, with the coupler substances generally used for oxidation hair coloring, various highly intensive color shades. In addition, the tetraaminopyrimidines are characterized by very good fastness properties of the colorings achieved, by good solubility in water, by good storability, and toxicological and dermatological harmlessness.

It has now been found that the 3,5-diamino-2-substituted alkyl benzenes, when used as coupler components according to the invention, are highly suitable as special yellow couplers for the tetraaminopyrimidine developer system and as special red couplers for the p-toluene-diamine developer system. Of particular advantage is the fact that the thermal stability of the yellow, brown and red dyes formed is substantially improved, as compared to that of a dye produced with other couplers. Furthermore, the dyes produced with the coupler substances according to the invention are characterized by particularly good fastness to light. In addition, intensive hair colors are also obtained by using the 3,5-diamino-2-substituted alkyl benzenes with other conventional developer components and the resulting dyes are furthermore characterized by excellent fastness to light and good penetrating power.

The present invention is more particularly directed to an aqueous preparation for the dyeing of hair consisting essentially of (1) from 0.2% to 5% by weight of an oxidation dyestuff combination of a developer component and a coupler component, said coupler component consisting essentially of (A) at least one 3,5-diamino-2-substituted-alkyl benzene of the formula

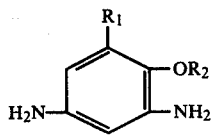

wherein $R_1$ is a straight- or branched-chain alkyl radical of 1 to 8 carbon atoms, and $R_2$ is a member selected from the group consisting of a straight- or branched-chain alkyl radical of 1 to 8 carbon atoms, phenyl, and phenyl substituted by a member selected from the group consisting of alkyl radicals of 1 to 4 carbon atoms and halogen atoms and (B) a water-soluble acid addition salt of (A); (2) from 0% to 5% by weight of a direct dyestuff; (3) from 0% to 30% by weight of a surfactant; (4) from 0% to 25% by weight of thickeners; and (5) the balance up to 100% by weight of water.

In the hair dyes according to the invention, the coupler components are generally used in substantially equimolar amounts, related to the developer substances used. Although equimolar amounts are advisable, it is possible to use more or less of either component in a certain excess or deficiency, as for example the molar range of 2:1 to 1:2, more preferably up a 10% excess or deficiency.

Furthermore, the developer component and the coupling component may be used as pure ingredients or as mixtures. Not only can the developer component consist of mixtures, but the coupler substance can also consist of mixtures of the above-mentioned 3,5-diamino-2-substituted-alkyl benzenes.

In addition, the hair coloring preparations according to the invention can contain admixtures of other customary developing components. Besides developer and/or coupler components they, if necessary, also contain the customary direct dyestuffs in case the latter are needed for obtaining certain shades. From 0% to 5% direct dyestuffs may be employed. Some examples of such other customary developers are p-phenylene diamine derivatives, diaminopyridines 4-aminopyrazolone derivatives and heterocyclic hydrazones. Some examples of such other customary couplers are m-phenylene diamine derivatives, phenols, naphthols, resorcinol derivatives and pyrazolones. Besides these, yet other such conventional developers and couplers will be readily perceived by those skilled in art.

As in the case of other oxidation hair dyes, the oxidative coupling, i.e., the developing of the dye, can in principle be effected by atmospheric oxygen. However, it is advantageous to use chemical oxidizing agents. Suitable examples are especially hydrogen peroxide or its products of addition to urea, melamine and sodium borate, as well as mixtures of such hydrogen peroxide addition products with potassium peroxydisulfate.

As developer components the tetraaminopyrimidines according to the invention have the advantage that they readily yield fully satisfactory hair dyeing results in oxidative coupling with atmospheric oxygen. Thus hair damage by the oxidizing agents, otherwise used in oxidative coupling, can be avoided. But if a brightening or bleaching effect is desired in the hair, in addition to the coloring effect, then the concurrent use of chemical oxidizing agents is necessary.

For the application, the hair dyes according to the invention are incorporated into suitable aqueous cosmetic preparations, such as creams, emulsions, gels or even simple solutions and immediately before application to the hair, one of the above-mentioned oxidizing agents is added. These hair dyeing compositions contain coupling and developing components in amounts of from 0.2% to 5% by weight, preferably from 1% to 3% by weight.

For the preparation of creams, emulsions or gels, the dye components are mixed with the additional ingredients customarily used in such preparations. Such additional ingredients are, for example, wetting agents or emulsifiers of the anionic or nonionic type, such as alkylbenzenesulfonates, higher fatty alcohol sulfates, higher alkylsulfonates, higher fatty acid alkanolamides, addition products of ethylene oxide on higher fatty alcohols, thickeners, such as methyl cellulose, starch, higher fatty alcohols, paraffin oil and higher fatty acids.

Furthermore, perfumes and hair-conditioning and grooming agents, such as pantothenic acid and cholesterol may be included.

Effective amounts of the above-mentioned additives are those customarily employed for this purpose. For example, effective amounts of wetting agents and emulsifiers range from 0.5% to 30% by weight, preferably from 1% to 15% by weight; and for thickeners, an effective amount ranges from 0.1% to 25% by weight, preferably from 1% to 15% by weight, based in each case on the total weight of the preparation. As a lower limit for the above additives, a zero percent lower limit is possible, if none of the additive is utilized.

The hair coloring preparations according to the invention can be applied in a weakly acid medium, a neutral medium or especially in an alkaline medium, preferably at a pH of 8 to 10, regardless of whether a solution, an emulsion, a cream, or a gel is employed.

These preparations are applied at a temperature which usually ranges from 15° C. to 40° C. and preferably is room temperature.

After the preparation has been allowed to react for about 30 minutes, the hair coloring preparation is removed from the hair to be dyed, by rinsing. Then the hair is washed with a mild shampoo, and finally is dried.

The following examples are merely illustrative of the present invention without being deemed limitative in any manner thereof.

EXAMPLES

The following examples describe the preparation of the 3,5-diamino alkyl benzenes substituted in the 2-position, which are used as coupler components in the hair dyes according to the invention.

EXAMPLE 1

Product K 1:
3,5-diamino-2-methoxytoluene-dihydrochloride 17.8 gm of 3,5-dinitro-2-methoxytoluene, prepared according to the procedure in the *Journal of the Chemical Society*, Vol. 123, p. 2263, were suspended in 100 ml of ethanol and reduced in the presence of 1 gm of catalyst (5% palladium on carbon) in a shaking vessel. After the hydrogen absorption was completed, the mixture was filtered off from the catalyst, dilute hydrochloric acid was added to it, and the mixture was concentrated. 17.4 gm of 3,5-diamino-2-methoxy-toluene-dihydrochloride with a decomposition point of 218°–226° C. were obtained.

| Elemental Analysis: | | | | |
|---|---|---|---|---|
| | %C | %H | %N | %Cl |
| Calculated: | 42.7 | 6.3 | 12.4 | 31.5 |
| Found: | 42.6 | 6.3 | 12.0 | 29.5 |

EXAMPLE 2

Product K 2:
3,5-diamino-2-ethoxytoluene-dihydrochloride 39.6 gm of 3,5-dinitro-2-ethoxytoluene, prepared according to the procedure in *Annalen der Chemie*, Vol. 217, p. 153 and 188, were reduced in 200 ml of ethanol in the presence of 1.5 gm of catalyst (5% palladium on carbon) at room temperature in a shaking vessel. After the hydrogen absorption was completed, the mixture was filtered off from the catalyst and acidified with dilute hydrochloric acid.

The precipitate was filtered off and dried. 8.6 gm of 3,5-diamino-2-ethoxytoluene-dihydrochloride in the form of red crystals with a melting point of 228° C. were obtained.

| Elemental Analysis: | | | | |
|---|---|---|---|---|
| | %C | %H | %N | %Cl |
| Calculated: | 45.2 | 6.7 | 11.7 | 29.7 |
| Found: | 45.2 | 6.9 | 11.8 | 28.9 |

EXAMPLE 3

Product K 3: 3,5-diamino-2-methoxyethyl benzene-dihydrochloride (A) 3,5-dinitro-2-methoxyethyl benzene 29 gm of 2-methoxyethylbenzene were slowly added in drops to 290 ml of fuming nitric acid, cooled to 5° C. (D=1.5). The temperature was maintained below 10° C. After stirring for 15 minutes, the mixture was poured on ice. The precipitate obtained was filtered off, washed with water, and dried. 31 gm of yellow crystals with a melting point of 65° C. were obtained.

(B) 3,5-diamino-2-methoxyethylbenzene-dihydrochloride 31.2 gm of 3,5-dinitro-2-methoxyethylbenzene, obtained as described above, were reduced at room temperature in 200 ml of ethanol in the presence of 1.5 gm of catalyst (5% palladium on carbon). After the hydrogen absorption was completed, the mixture was filtered off from the catalyst and acidified with dilute hydrochloric acid. The precipitate then was filtered off and dried. There was obtained 30 gm of 3,5-diamino-2-methoxyethylbenzene-dihydrochloride having 1½ moles of water of crystallization in the form of yellow crystals with a melting point of 214° C.

| Elemental Analysis: | | | | |
|---|---|---|---|---|
| | %C | %H | %N | %Cl |
| Calculated: | 40.6 | 7.2 | 10.5 | 26.6 |
| Found: | 40.2 | 7.2 | 11.1 | 25.9 |

In the following examples, the above-mentioned 3,5-diamino-alkyl benzenes substituted in the 2-position were used as coupler components. Said coupler components are:

K 1: 3,5-diamino-2-methoxytoluene-dihydrochloride
K 2: 3,5-diamino-2-ethoxy toluene-dihydrochloride
K 3: 3,5-diamino-2-methoxyethyl benzene-dihydrochloride As developer components were used the following compounds:

E 1: 2,4,5,6-tetraaminopyrimidine
E 2: 2-dimethylamino-4,5,6-triaminopyrimidine
E 3: 2-morpholino-4,5,6-triaminopyrimidine
E 4: 2,4-bis-dimethylamino-5,6-diaminopyrimidine
E 5: p-toluenediamine
E 6: p-phenylenediamine
E 7: p-aminophenol

EXAMPLE 4

The hair dyes according to the invention were used in the form of a cream emulsion. The emulsion contained 10 parts by weight of fatty alcohols having 12 to 18 carbon atoms, 10 parts by weight of fatty alcohol sulfate (sodium salt) having 12 to 18 carbon atoms and 75 parts by weight of water.

Into each emulsion, there were incorporated 0.01 mole of the developer substances and 0.01 mole of the 3,5-diamino-2-substituted-alkyl benzenes, which are listed in the following Table. Then, the pH-value of the emulsion was adjusted with ammonia to 9.5, and the emulsion was made up to 100 parts by weight with water. The oxidative coupling was effected by using as an oxidizing agent either atmospheric oxygen or a 1% hydrogen peroxide solution, 10 parts by weight hydrogen peroxide solution being added to 100 parts by weight of the emulsion. The respective creams, with or without additional oxidizing agents, were applied to human hair that was 90% gray and that had not been pretreated in a special manner. After the cream had remained on the hair for 30 minutes to complete the dyeing process, the hair was washed with an ordinary shampoo and then dried. The shades thereby obtained are also listed in the following Table.

Following are additional examples of the 3,5-diamino-2-substituted-alkyl benzene coupling components of the present invention.

EXAMPLE 5

Product K 4:
3,5-diamino-2-octyloxytoluene-dihydrochloride

A: 3,5-dinitro-2-octyloxytoluene 60 gm of n-octyl-o-tolylether were added slowly dropwise to 500 ml of nitric acid, cooled to 5° C. (D=1.5). The temperature was kept below 10° C. After stirring for 15 minutes, the mixture was poured on ice. The separated oil was extracted with 3×300 ml of ethyl acetate. After drying (over $Na_2SO_4$), the mixture was concentrated to dryness. 66.5 gm of an oily residue were obtained.

Characteristic Values

Rf (silica gel, $CHCl_3:C_2H_5OH=9:1$): 0.77. Infrared Spectrum ($cm^{-1}$): 3100, 2960, 2930, 2880, 1740, 1630, 1600, 1535, 1468, 1340, 1280, 1262, 1240, 1220, 1090, 1045, 960, 930, 905, 860, 800, 748, 690.

B: 3,5-diamino-2-octyloxytoluene-dihydrochloride 5 gm of 3,5-dinitro-2-octyloxytoluene, obtained as described above, were reduced at room temperature in 100 ml of ethanol in the presence of 1 gm of catalyst (5% palladium on carbon). After the hydrogen absorption was completed, the mixture was filtered off from the catalyst and acidified with dilute hydrochloric acid. The precipitate was filtered off and dried. There was obtained 1.5 gm of 3,5-diamino-2-octyloxytoluene-dihydrochloride having 0.5 mole of water of crystallization in the form of yellow crystals with a melting point of 160° C.

Elemental Analysis:

|  | %C | %H | %N |
|---|---|---|---|
| Calculated: | 54.2 | 8.7 | 8.4 |
| Found: | 54.3 | 8.8 | 8.4 |

EXAMPLE 6

Product K 5:
3,5-diamino-2-phenyloxytoluene-dihydrochloride

A: 3,5-dinitro-2-phenyloxytoluene

A mixture of 6 gm of 3,5-dinitro-2-bromotoluene and 3 gm of potassium phenolate in 20 ml of dimethyl formamide was boiled under reflux for 20 hours. Subsequently, the solution was poured on 200 gm of ice and the precipitate was filtered off. After recrystallization from ethanol, there was obtained 1.1 gm of yellow crystals with a melting point of 103° C. The mass spectrum showed a molecular mass of 274 (calculated 274).

B: 3,5-diamino-2-phenyloxytoluene-dihydrochloride 1.0 gm of 3,5-dinitro-2-phenyloxytoluene, obtained as described above, were reduced at room temperature in 30 ml of ethanol in the presence of 0.3 gm of catalyst (5% palladium on carbon). After the hydrogen absorption was completed the mixture was filtered off from the catalyst and acidified with dilute hydrochloric acid. The precipitate was filtered off and dried. There was obtained 0.4 gm of 3,5-diamino-2-phenyloxytoluene-dihydrochloride with 1.5 moles of water of crystallization in the form of yellow crystals with a decomposition point of 167° C. The mass spectrum showed a molecular mass of 215 (calculated 214).

Elemental Analysis:

|  | %C | %H |
|---|---|---|
| Calculated | 49.7 | 6.1 |
| Found | 49.8 | 6.5 |

Dyeing of 90% gray hair by means of a cream emulsion as described above, using the above coupling compounds K4 and K5 and 2,4,5,6-tetraaminopyrimidine (E1) yielded the shades presented in Examples 24 and 25 of the following Table.

TABLE

| Ex. | Developer | Coupler | Shade Obtained With Atmospheric Oxygen | With 1% $H_2O_2$ Solution |
|---|---|---|---|---|
| 7 | E1 | K1 | honey yellow | honey yellow |
| 8 | E2 | K1 | yellow brown | golden brown |
| 9 | E3 | K1 | olive brown | brass yellow |
| 10 | E4 | K1 | golden brown | golden brown |
| 11 | E5 | K1 | light brown | mahogany brown |
| 12 | E6 | K1 | light brown | dark brown |
| 13 | E7 | K1 | light brown | light brown |
| 14 | E1 | K2 | honey yellow | yellow brown |
| 15 | E2 | K2 | yellow brown | golden brown |
| 16 | E3 | K2 | golden brown | honey yellow |
| 17 | E4 | K2 | brown-orange | brown-orange |
| 18 | E5 | K2 | light brown | brown |
| 19 | E1 | K3 | deep yellow | deep yellow |
| 20 | E2 | K3 | golden brown | golden brown |
| 21 | E3 | K3 | golden brown | honey yellow |
| 22 | E4 | K3 | brown-orange | brown-orange |
| 23 | E5 | K3 | red-brown | red-brown |
| 24 | E1 | K4 | honey yellow | honey yellow |
| 25 | E1 | K5 | yellow | yellow |

We claim:

1. An aqueous preparation of the developer-coupler type for the dyeing of hair, consisting essentially of
   (a) 0.2 to 5% by weight of a developer-coupler combination of, as a coupler,
      (A) a 3,5-diamino-2-substituted alkyl benzene of the formula

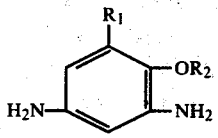

wherein $R_1$ is a straight- or branched-chain alkyl of 1 to 8 carbon atoms and $R_2$ is a member selected from the group consisting of a straight- or branched-chain alkyl radical of 1 to 8 carbon atoms, phenyl, and phenyl substituted by a member selected from the group consisting of alkyl radicals of 1 to 4 carbon atoms and halogen atoms, or (B) a water-soluble acid addition salt of (A), and a conventional developer therefor, said coupler and said developer being present in the molar range of about 2:1 to 1:2;

(b) 0% to 30% by weight of a surfactant;

(c) 0% to 25% by weight of a thickener; and (d) the remainder water.

2. The preparation of claim 1, wherein $R_1$ and $R_2$ are alkyl radicals of 1 to 4 carbon atoms.

3. The preparation of claim 1 wherein $R_1$ is an alkyl radical of 1 to 4 carbon atoms and $R_2$ is phenyl.

4. The preparation of claim 1 wherein $R_1$ is an alkyl radical of 1 to 4 carbon atoms and $R_2$ is phenyl substituted by a member selected from the group consisting of alkyl radicals of 1 to 4 carbon atoms and halogen atoms.

5. The preparation of claim 1 wherein $R_1$ is an alkyl radical of 1 to 4 carbon atoms and $R_2$ is an alkyl radical of 4 to 8 carbon atoms.

6. The preparation of claim 1 wherein the coupler is 3,5-diamino-2-methoxytoluene.

7. The preparation of claim 1 wherein the coupler is in the form of a dermatologically-acceptable water-soluble salt.

8. The preparation of claim 1 wherein the developer is (A) a tetraaminopyrimidine of the formula

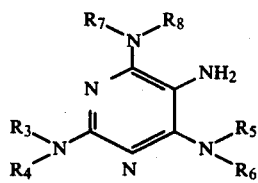

wherein $R_3$, $R_4$, $R_5$, $R_6$, $R_7$ and $R_8$ are each selected from the group consisting of hydrogen, phenyl, alkyl having 1 to 4 carbon atoms, phenylalkyl having 7 to 10 carbon atoms, phenylalkenyl having 7 to 10 carbon atoms, $$X-(CH_2)_n-$$

wherein n is an integer from 1 to 4, and X is selected from the group consisting of hydroxyl, halogen and $NR_9R_{10}$— in which $R_9$ and $R_{10}$ are each independently hydrogen or alkyl having 1 to 4 carbon atoms, and together with the nitrogen atom $R_9$ and $R_{10}$ can form a heterocyclic ring optionally containing an additional nitrogen atom or oxygen atom, and wherein $R_3$ and $R_4$, $R_5$ and $R_6$, and $R_7$ and $R_8$, together with the nitrogen atom can form a five to six membered heterocyclic ring optionally containing another nitrogen or oxygen atom in the ring and (B) a water-soluble acid addition salt of (A).

9. The preparation of claim 8, wherein in the developer $R_3$, $R_4$, $R_5$, $R_6$, $R_7$ and $R_8$ are each selected from the group consisting of hydrogen, methyl, ethyl, isopropyl, n-propyl, butyl, phenyl, benzyl, benzylidene and —$(CH_2)_n$—X, and wherein $R_3$ and $R_4$, or $R_5$ and $R_6$, or $R_7$ and $R_8$, together with the nitrogen atom form a substituent selected from the group consisting of piperidino and morpholino; and wherein n is 1, 2 or 3 and X is selected from the group consisting of hydroxyl, halogen and —$NR_9R_{10}$ in which $R_9$ and $R_{10}$ are each hydrogen or alkyl having 1 to 4 carbon atoms.

10. The preparation of claim 8 wherein the coupler is selected from the group consisting of 3,5-diamino-2-methoxytoluene, 3,5-diamino-2-ethoxytoluene, 3,5-diamino-2-methoxyethyl-benzene, 3,5-diamino-2-octyloxytoluene, 3,5-diamino-2-phenyloxytoluene, and the water-soluble acid addition salts of the above couplers, and the developer is selected from the group consisting of 2,4,5,6-tetraaminopyrimidine, 2-dimethylamino-4,5,6-triaminopyrimidine, 2-morpholino-4,5,6-triaminopyrimidine, 2,4-bis-dimethylamino-5,6-diaminopyrimidine, and the water-soluble acid addition salts of the above developers.

11. The preparation of claim 1 wherein the developer is p-toluenediamine.

12. The preparation of claim 1 wherein $R_1$ and $R_2$ are alkyl radicals of 1 to 4 carbon atoms and the developer is selected from the group consisting of p-toluenediamine, p-phenylene-diamine and p-aminophenol.

13. The preparation of claim 1 which contains 1% to 3% by weight of the developer-coupler combination.

14. A process for the dyeing of hair comprising applying to said hair, at temperatures ranging substantially from 15° C. to 40° C. for a time sufficient to effect dyeing through atmospheric oxidation, an effective amount of the preparation of claim 1.

15. The process for the dyeing of hair of claim 14 wherein the oxidation is also effected by the action of a chemical oxidizing agent.

16. A compound selected from the group consisting of (A) a 3,5-diamino-2-substituted alkyl benzene of the formula

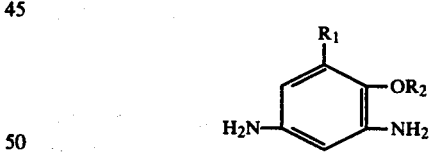

wherein $R_1$ is a straight- or branched-chain alkyl radical of 1 to 8 carbon atoms and $R_2$ is a member selected from the group consisting of phenyl and phenyl substituted by a member selected from the group consisting of alkyl radicals of 1 to 4 carbon atoms and halogen atoms and (B) a water-soluble acid addition salt of A.

17. The compound of claim 16 wherein $R_1$ is an alkyl radical of 1 to 4 carbon atoms and $R_2$ is phenyl.

18. The compound of claim 16 wherein $R_1$ is an alkyl radical of 1 to 4 carbon atoms and $R_2$ is phenyl substituted by a member selected from the group consisting of alkyl radicals of 1 to 4 carbon atoms and halogen atoms.

19. The compound of claim 16 which is the water-soluble acid addition salt of (A).

20. The compound of claim 16 which is 3,5-diamino-2-phenyloxytoluene.

* * * * *

UNITED STATES PATENT AND TRADEMARK OFFICE
CERTIFICATE OF CORRECTION

PATENT NO. : 4,171,203
DATED : October 16, 1979
INVENTOR(S) : DAVID ROSE et al.

It is certified that error appears in the above—identified patent and that said Letters Patent are hereby corrected as shown below:

ABSTRACT, line 13, "tie" should read -- time --.

Column 3, lines 41-47 and Column 11, lines 43-49, the formula in each instance should read:

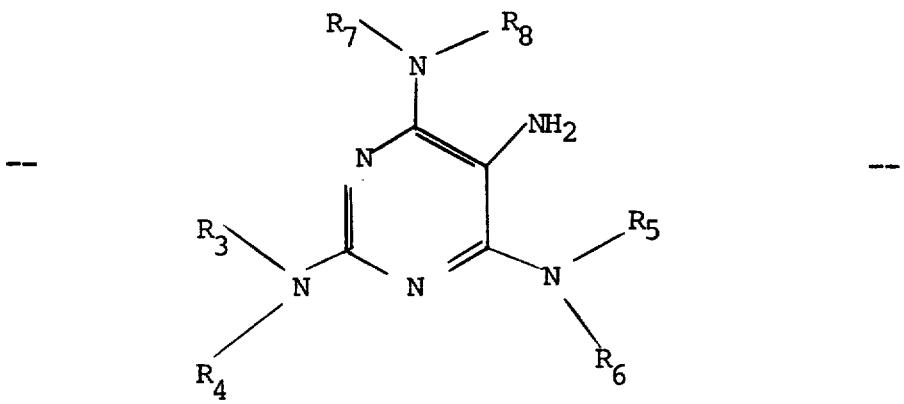

Signed and Sealed this

Fifteenth Day of April 1980

[SEAL]

Attest:

SIDNEY A. DIAMOND

Attesting Officer   Commissioner of Patents and Trademarks